United States Patent [19]
Behler et al.

[11] Patent Number: 5,294,726
[45] Date of Patent: Mar. 15, 1994

[54] PROCESS FOR THE PREPARATION OF LIGHT-COLORED OLEIC ACID SULFONATES

[75] Inventors: Ansgar Behler, Bottrop; Hermann Anzinger; Michael Vogt, both of Duesseldorf, all of Fed. Rep. of Germany

[73] Assignee: Henkel Kommanditgesellschaft auf Aktien, Duesseldorf, Fed. Rep. of Germany

[21] Appl. No.: 834,252

[22] PCT Filed: Jul. 31, 1990

[86] PCT No.: PCT/EP90/01248

§ 371 Date: Feb. 10, 1992

§ 102(e) Date: Feb. 10, 1992

[87] PCT Pub. No.: WO91/01972

PCT Pub. Date: Feb. 21, 1991

[30] Foreign Application Priority Data

Aug. 9, 1989 [DE] Fed. Rep. of Germany ....... 3926344

[51] Int. Cl.$^5$ ................................................ C11D 1/28

[52] U.S. Cl. ...................................................... 554/98
[58] Field of Search ......................................... 554/98

[56] References Cited

FOREIGN PATENT DOCUMENTS 1278421  6/1972  United Kingdom .

*Primary Examiner*—José G. Dees
*Assistant Examiner*—Deborah D. Carr
*Attorney, Agent, or Firm*—Ernest G. Szoke; Wayne C. Jaeschke; Henry E. Millson, Jr.

[57] ABSTRACT

A process for the preparation of light-colored oleic acid sulfonates by continuous sulfonation of an industrial oleic acid having an oleic acid content of 65 to 85% by weight and a linoleic acid content of up to 13% by weight with gaseous sulfur trioxide in a molar ratio of industrial oleic acid to sulfur trioxide of 1 : 0.8 to 1 : 1.0, neutralization and hydrolysis of the acid sulfonation product with aqueous bases and bleaching of the neutralized and hydrolyzed sulfonation product give oleic acid sulfonates having Klett color numbers of not more than 100.

19 Claims, No Drawings

PROCESS FOR THE PREPARATION OF LIGHT-COLORED OLEIC ACID SULFONATES

BACKGROUND OF THE INVENTION

1. Field of the Invention

The invention relates to a process for the preparation of light-colored oleic acid sulfonates.

2. Description of Related Art

The preparation of oleic acid sulfonates by reaction of industrial oleic acid cuts with gaseous sulfur trioxide is known from GB-C 1,278,421. This publication makes the following statements on the color of the oleic acid sulfonates obtained by this process: 1. The color of the sulfonation products depends on the reaction conditions, in particular the contact time in the reactor and the temperature of the starting substances fed to the reactor. 2. The color of the sulfonation products depends on the amount of sulfur trioxide employed, an excess of more than 15 mol %, based on oleic acid, resulting in poorer colors with only a slight increase in the degree of conversion. 3. The color of the sulfonation products depends on the content of polyunsaturated fatty acids in the industrial oleic acid employed, a content of more than 3% of these polyunsaturated fatty acids leading to poor colors of the sulfonation products.

There are available on the market numerous industrial oleic acid grades, in particular those of regenerating naturally occurring raw materials, such as beef tallow, lard, olive oil, sunflower oil and palmkernel oil, which have contents of polyunsaturated fatty acids of more than 3% and to date could not be sulfonated by the process known from GB-PC 1,278,421 to form light-colored oleic acid sulfonates.

DESCRIPTION OF THE INVENTION

The process of the invention is thus directed towards the preparation of light-colored oleic acid sulfonates which can be obtained from industrial oleic acid grades having a relatively high content of polyunsaturated fatty acids using gaseous sulfur trioxide as the sulfonating agent.

The process of the invention comprises the following stages:

a) continuous sulfonation of an industrial oleic acid having an oleic acid content of 65 to 85% by weight and a linoleic acid content of up to 13% by weight, the remainder (to 100% by weight) being other saturated or unsaturated fatty acids having 10 to 22 carbon atoms, using gaseous sulfur trioxide in a molar ratio of olefinic double bonds present in the industrial oleic acid to sulfur trioxide of 1 : 0.8 to 1.0;

b) neutralization and hydrolysis of the acid sulfonation product obtained in stage a) with aqueous bases and c) bleaching of the oleic acid sulfonate obtained in stage b) as an aqueous solution, and if appropriate d) concentration of the aqueous solution, obtained in stage c), of the bleached oleic acid sulfonate.

The industrial oleic acid to be employed in the process of the invention contains other saturated or unsaturated fatty acids having 10 to 22 carbon atoms, that is to say fatty acids which are not oleic acid or linoleic acid and which are usually contained as concomitant substances in industrial oleic acid grades, for example capric, lauric, myristic, myristoleic, palmitic, palmitoleic, stearic, linolenic, arachinic, gadoleic, behenic and erucic acid. Fatty acids which are diunsaturated and more than di-unsaturated and are not linoleic acid can be contained in an amount which is preferably not more than 2% by weight.

According to the process of the invention, the acid sulfonation product obtained in the above-mentioned stage a) is neutralized and hydrolyzed with aqueous bases. During this procedure, the sulfonic acid groups formed during the sulfonation reaction react to form the corresponding salts; sultones which are possibly formed are furthermore hydrolyzed in the course of the sulfonation. Typical examples of the aqueous bases which can be employed in the neutralization and sulfonation are aqueous solutions of hydroxides of alkali metals, such as sodium, potassium or lithium, or of oxides and hyroxides of alkaline earth metals, such as magnesium or calcium, ammonia or organic bases, such as ethanolamine, diethanolamine or triethanolamine. The use of aqueous sodium hydroxide solution is in general preferred.

According to the process of the invention, the oleic acid sulfonate obtained in stage b) is bleached; the methods customary for the bleaching of surface-active sulfonates and sulfates can be used here. It is possible, and also advantageous for processes on an industrial scale, for the stages of neutralization and hydrolysis and of bleaching to be carried out simultaneously. The bleached reaction product can then, if desired, be concentrated by removal of water, for example by distillation.

On the basis of the prior art discussed at the outset, it was not to have been expected that the sulfonation of industrial oleic acid grades having a linoleic acid content of up to 13% by weight, in particular in the range from 4 to 12% by weight, based on the total weight of the industrial oleic acid, enables bleachable oleic acid sulfonates to be prepared.

According to a preferred embodiment of the process of the invention, an industrial oleic acid which has a linoleic acid content in the range from 4 to 13% by weight, based on the total weight of the industrial oleic acid, is sulfonated.

According to another advantageous embodiment of the invention, the industrial oleic acid is sulfonated with the gaseous sulfur trioxide in a molar ratio of olefinic double bonds present in the industrial oleic acid to sulfur trioxide in the range from 1 : 0.90 to 0.98. Within this range, particularly light-colored oleic acid sulfonates can be obtained after bleaching.

The sulfonation stage of the process of the invention can be carried out in the customary reactors for the reaction of suitable reactants with gaseous sulfur trioxide; such reactors are described, for example, in G. Dieckelmann, H.J. Heinz, The Basics of Industrial Oleochemistry, Peter Pomp GmbH, pages 111 to 128 (1988). The sulfonation in reactors of the falling film reactor type is preferred. It is advantageous to use an inert gas containing 1 to 10% by volume of sulfur trioxide for the sulfonation. Preferred conditions for the sulfonation are reaction temperatures in the range from 40 to 80, in particular from 40 to 60° C.

According to another advantageous embodiment of the invention, the acid sulfonation products are neutralized and hydrolyzed at temperatures in the range from 60 to 95° C., in particular 80 to 90° C., preferably in the course of 1 to 8 hours at a pH in the range from 5 to 9.

According to another advantageous embodiment of the process of the invention, the neutralized and hydrolyzed sulfonation product is bleached with aqueous hydrogen peroxide solution. Solutions having a content of 20 to 90% by weight of hydrogen peroxide can be used here. In general, the hydrogen peroxide solution is employed in an amount of 1 to 4% by weight of hydrogen peroxide, based on the active substance content in the neutralized and hydrolyzed sulfonation product. The bleaching is preferably carried out in the pH range from 5 to 9.

To obtain light-colored oleic acid sulfonates, it has furthermore proved to be particularly advantageous for the starting substance employed to be a distilled industrial oleic acid which has been obtained, for example, from naturally occurring fats and oils by the hydrophilization process in combination with preceding or subsequent lipolysis, and which has been stored for not more than 1 month in contact with air after the distillation.

Industrial oleic acid sulfonates which have Klett color numbers of not more than 100, in particular of not more than 50, after bleaching can be prepared by means of the process of the invention.

The invention is thus based on the finding that the following measures - individually or in combination with one another - are of importance for obtaining light-colored oleic acid sulfonates by sulfonation of an industrial oleic acid with gaseous sulfur trioxide, neutralization and hydrolysis and bleaching:

a molar ratio of industrial oleic acid to sulfur trioxide of 1 : 0.8 to 1.0, in particular of 1 : 0.9 to 0.98, a linoleic acid content of not more than 13% by weight, in particular of 4 to 12% by weight;

an oleic acid grade which is as freshly distilled as possible and which should not be kept for longer than 1 month with access of air after the distillation;

bleaching with aqueous hydrogen peroxide solutions in an amount corresponding to 0. 5 to 4, in particular 1.0 to 2% by weight of hydrogen peroxide, based on the active substance in the resulting aqueous solutions of the oleic acid sulfonate.

The invention is illustrated in more detail below with the aid of preferred embodiments, reference being made to the table at the end of the description.

Table 1 contains, for 7 different commercially available industrial oleic acid grades to be employed according to the invention, the compositions (in percentage areas) determined by gas chromatography, the acid number (AN) and the iodine number (IN); and furthermore the Klett color number after bleaching. The table furthermore contains the corresponding values for an oleic acid A employed for comparison purposes and having a linoleic acid content which lies outside the range claimed.

The fatty acids determined in the industrial oleic acid grades employed are reproduced in an abbreviated notation. The subscript after the letter C denotes the number of carbon atoms in the chain; the number of primes denotes the number of olefinic double bonds present in the chain. Thus, for example, $C_{18}$ denotes stearic acid, $C_{18}'$ oleic acid, $C_{18}''$ linoleic acid and $C_{18}'''$ linolenic acid.

The oleic acid grades No. 1 to 7 and A employed were of the following origin:
No. 1: from beef tallow,
No. 2: from olive oil,
No. 3: from sunflower oil,
No. 4: from palm-kernel oil,
No. 5: from olive oil,
No. 6: from beef tallow,
No. 7: from beef tallow,
A: from rape seed oil.

The abovementioned oleic acid grades are commercially available products.

General working instructions for the sulfonation of industrial oleic acid.

The sulfonations were carried out in a falling film reactor of glass, which essentially consisted of a tube 1,100 mm long and 6 mm in internal diameter surrounded by a heating and cooling jacket. The reactor was provided at the top with a device for introducing the oleic acid and with a gas inlet tube. Gaseous sulfur trioxide produced by heating oleum was diluted with nitrogen to a concentration of 5% by volume of sulfur trioxide and was employed for the sulfonation.

The oleic acid was introduced at a constant rate of 550 g/hour. The feed of the sulfur trioxide/nitrogen mixture was adjusted so that the molar ratio of olefinic double bonds present in the industrial oleic acid (calculated from the iodine number) to sulfur trioxide was 1: 0.90. The reaction temperature of the sulfonation was kept at 50° C. with the aid of a water circulation through the reactor jacket.

After leaving the reactor, the reaction mixture was collected in a glass beaker which contained a 25% by weight sodium hydroxide solution and then heated at 90° C. at a pH of 8 to 9 for two hours.

Two % by weight of hydrogen peroxide, based on the active substance and added in the form of a 35% strength by weight aqueous hydrogen peroxide solution, were added in portions to the hydrolyzed product at ambient temperature (about 20° C.).

Bleached, pale yellow products dissolved in water to give a clear solution were obtained. The product obtained with oleic acid No. 4 according to Table 1 had the following characteristics:

| | |
|---|---|
| washing active substance (according to Epton, see Nature 160 (1947), 759 and Tenside 4 (1967), 292; molecular weight = 405): | 37.0% |
| non-sulfonatable substance (petroleum ether extract): | 4.5% |
| sodium sulfate: | 1.1% |
| dry residue: | 46.1% |
| Klett color number (1 cm circular cell): | 12 |

The Klett color number was determined in a Klett-Summerson photometer with a blue filter (400 to 450 nm) using 1 cm circular cells with an aqueous solution containing 5% by weight of washing active substance.

The Klett color numbers obtained with the abovementioned oleic acid grades after different storage times and with different molar ratios of double bonds present in the oleic acid mixture employed to sulfur trioxide are summarized in Table 2 at the end of the description. The experiments with oleic acid No. 6 show that a storage time of six months leads to considerably poorer Klett color numbers in comparison with freshly distilled oleic acid (storage time =0 months). A storage time of more than one month (with access of air) already leads to a noticeable deterioration in the Klett color number. As shown by the experiment with the industrial oleic acid A, oleic acid grades having a linoleic acid content of more than 13% give oleic acid sulfonates which can no longer be bleached.

TABLE 1

Industrial oleic acids employed

| Oleic acid No. Composition | 1 | 2 | 3 | 4 | 5 | 6 | 7 | A |
|---|---|---|---|---|---|---|---|---|
| $C_{12}$ | 0.1 | — | — | 0.5 | — | 0.4 | 0.2 | — |
| $C_{14}$ | 2.7 | 0.1 | <0.5 | 1.2 | — | 2.1 | 2.6 | |
| | | | | | | | | 0.5 |
| $C_{14}'$ | 0.8 | — | — | — | — | 0.3 | 2.4 | |
| $C_{15}$ | 0.5 | — | — | — | — | 0.4 | 0.4 | — |
| $C_{16}$ | 4.1 | 16.2 | 3.5 | 4.3 | 4.6 | 4.6 | 3.7 | 5.5 |
| $C_{16}'$ | 5.4 | 1.1 | <1 | 0.3 | 1.0 | 5.0 | 10.3 | — |
| $C_{17}$ | 1.3 | 0.2 | <1 | 0.4 | 0.2 | 1.2 | 2.5 | — |
| $C_{18}$ | 1.0 | 2.3 | 3.6 | 1.0 | 1.6 | 0.9 | 0.9 | 1.5 |
| $C_{18}'$ | 73.3 | 68.7 | 82.8 | 80.0 | 82.7 | 70.7 | 72.6 | 56 |
| $C_{18}''$ | 8.7 | 10.1 | 8.4 | 11.0 | 8.1 | 11.8 | 2.7 | 21.5 |
| $C_{18}'''$ | 1.0 | 0.5 | <1 | 0.2 | 0.7 | 0.6 | 0.5 | 10.5 |
| $C_{20}$ | 0.1 | 0.3 | 0.1 | 0.2 | 0.3 | 0.2 | 0.2 | 0.5 |
| $C_{20}'$ | 1.1 | 0.4 | <1 | 0.2 | 0.3 | 1.8 | 1.0 | 1.5 |
| AM | 201.7 | 200.0 | 196.3 | 199.8 | 194.7 | 200.4 | 202.7 | 199 |
| IM | 93.5 | 85.1 | 86.5 | 92.5 | 92.3 | 93.8 | 85.2 | 122 |

TABLE 2

Influence of storage times and molar ratios on the Klett color number

| from oleic acid no. | Storage time (months) | Molar ratio C=C:SO$_3$ | Degree of sulfonation (%) | Klett color number |
|---|---|---|---|---|
| 1 | 0 | 0.98 | 86.4 | 36 |
| 1 | 1 | 1.0 | 90.2 | 38 |
| 1 | 2 | 0.90 | 87.1 | 46 |
| 2 | 0 | 0.94 | 81.5 | 21 |
| 3 | 0 | 0.94 | 85.7 | 19 |
| 4 | 0 | 0.97 | 90.1 | 39 |
| 4 | 0 | 0.94 | 86.2 | 12 |
| 5 | 0 | 0.91 | 85.0 | 23 |
| 6 | 0 | 0.92 | 87.0 | 45 |
| 6 | 6 | 0.90 | 84.5 | 98 |
| 6 | 6 | 0.97 | 88.6 | 165 |
| 7 | 0 | 0.94 | 83.5 | 10 |
| A | 0 | 0.94 | 90.5 | >600 |

We claim:

1. A process for the preparation of oleic acid sulfonate having a Klett color number of not more than 100 from oleic acid containing relatively large quantities of linoleic acid comprising the steps of
   A. continuously sulfonating crude oleic acid having an oleic acid content in the range of from about 65 to about 85% by weight, a linoleic acid content of from about 4 to about 13% by weight, and wherein the remainder of the crude oleic acid is comprised predominantly of other saturated and/or unsaturated fatty acids having from 10 to 22 carbon atoms, and wherein the crude oleic acid is distilled industrial oleic acid which has not been stored in air following distillation for more than one month, with gaseous sulfur trioxide in a molar ratio of olefinic double bonds present in the crude oleic acid to sulfur trioxide of about 1:0.8 to 1.0 to form an acid sulfonation product;
   B. neutralizing and hydrolyzing the acid sulfonation product from step A with at least one aqueous base; and
   C. bleaching the resulting aqueous solution of oleic acid sulfonate with a bleaching agent to produce oleic acid sulfonate having a Klett color number of not more than 100.

2. The process of claim 1 wherein in step A said molar ratio is about 1:0.90 to 0.98.

3. The process of claim 1 wherein step A is carried out in a falling film reactor.

4. The process of claim 1 wherein step A is carried out using an inert gas containing from about 1 to about 10% by volume of sulfur trioxide.

5. The process of claim 1 wherein step A is carried out at a temperature in the range of from about 40 to about 80° C.

6. The process of claim 5 wherein said temperature is in the range of from about 40 to about 60° C.

7. The process of claim 1 wherein step B is carried out a temperature in the range of from about 80 to about 90° C.

8. The process of claim 7 wherein step B is carried out a temperature in the range of from about 80 to about 90° c.

9. The process of claim 1 wherein the bleached aqueous solution of oleic acid sulfonate from step C is concentrated by removal of water therefrom.

10. The process of claim 1 wherein step B is carried out over a period of from about 1 to about 8 hours.

11. The process of claim 1 wherein step B is carried out at a pH in the range of from about 5 to about 9.

12. The process of claim 1 wherein step B is carried out with an aqueous solution of an alkali metal hydroxide.

13. The process of claim 1 wherein step C is carried out with aqueous hydrogen peroxide solution.

14. The process of claim 1 wherein step C is carried out at a pH in the range of from about 5 to about 9.

15. The process of claim 1 wherein in step A the crude oleic acid has a linoleic acid content of from about 4 to about 12% by weight, in step A said molar ratio is about 1:0.90 to 0.98 and the reaction temperature is in the range of from about 40 to about 80° C., step B is carried out at a temperature in the range of from about 60 to about 95° C. and at a pH in the range of from about 5 to about 9 and with an aqeuous solution of an alkali metal hydroxide, and step C is carried out with an aqueous hydrogen peroxide solution.

16. The process of claim 15 wherein the temperature in step A is from about 40 to about 60° C., and the temperature in step B is from about 80 to about 90° C. and step B is carried out for a period of from about 1 to about 8 hours.

17. A process for the preparation of oleic acid sulfonate having Klett color number of not more than 100 from oleic acid containing relatively large quantities of linoleic acid comprising the steps of:

A. continuously sulfonating crude oleic acid having an oleic acid content in the range of from about 65 to about 85% by weight, a linoleic acid content of from about 4 to about 13% by weight, and wherein the remainder of the crude oleic acid is comprised predominantly of other saturated and/or unsaturated fatty acids having from 10 to 22 carbon atoms, and wherein the crude oleic acid is distilled industrial oleic acid which has not been stored in air following distillation for more than one month, with gaseous sulfur trioxide in a molar ratio of olefinic double bonds present in the crude oleic acid to sulfur trioxide to about 1:0.8 to 1.0 to form an acid sulfonation production;

B. simultaneously neutralizing, hydrolyzing, and bleaching the acid sulfonation product from step A with at least one aqueous base and a bleaching agent to produce oleic acid sulfonate having a Klett color number of not more than 100.

18. The process of claim 17 wherein step B is carried out with an aqueous alkali metal hydroxide and aqueous hydrogen peroxide.

19. The process of claim 17 wherein step B is carried out at a temperature in the range of from about 60 to about 95° C., at a pH in the range of from about 5 to about 9, and for a period of from about 1 to about 8 hours.

* * * * *

UNITED STATES PATENT AND TRADEMARK OFFICE
CERTIFICATE OF CORRECTION

PATENT NO. : 5,294,726
DATED : Mar. 15, 1994
INVENTOR(S) : Behler et. al.

It is certified that error appears in the above-indentified patent and that said Letters Patent is hereby corrected as shown below:

In claim 7, column 6, line 31, "80", should read:
-- 60 --.

In claim 7, column 6, line 32, "90°C", should read:
-- 95°C --.

Signed and Sealed this

Fourth Day of July, 1995

Attest:

BRUCE LEHMAN

Attesting Officer       Commissioner of Patents and Trademarks